United States Patent [19]

Waranis et al.

[11] Patent Number: 5,536,729
[45] Date of Patent: Jul. 16, 1996

[54] RAPAMYCIN FORMULATIONS FOR ORAL ADMINISTRATION

[75] Inventors: Robert P. Waranis, Chazy, N.Y.; Thomas W. Leonard, Willmington, N.C.

[73] Assignee: American Home Products Corporation, Madison, N.J.

[21] Appl. No.: 301,179

[22] Filed: Sep. 9, 1994

Related U.S. Application Data

[63] Continuation-in-part of Ser. No. 129,529, Sep. 30, 1993, abandoned.

[51] Int. Cl.[6] .................................................. A61K 31/445
[52] U.S. Cl. ........................................................... 514/291
[58] Field of Search ......................................... 514/291, 76

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,885,171 | 12/1989 | Surendra et al. | 424/122 |
| 5,080,899 | 1/1992 | Sturm et al. | 424/122 |
| 5,100,899 | 3/1992 | Caln | 514/291 |

FOREIGN PATENT DOCUMENTS

| | | |
|---|---|---|
| 0041795 | 12/1981 | European Pat. Off. . |
| 0428169 | 5/1991 | European Pat. Off. . |
| 0444659 | 9/1991 | European Pat. Off. . |

OTHER PUBLICATIONS

Physicians' Desk Reference, 45th ed., 1991, pp. 2119–2122, Medical Economics Company, Inc.
Physicians' Desk Reference, 45th ed., 1991, pp. 785–787, Medical Economics Company, Inc.
Luke et al., Effects of Cyclosporine on the Isolated Perfused Rat Kidney, Transplantation, vol. 43, No. 6, pp. 795–799, 1987.
Venkataram, et al., Pharmacokinetics of Two Alternative Dosage Forms for Cyclosporine: Liposomes and Intralipid, Journal of Pharmaceutical Sciences, vol. 79, No. 3, pp. 216–219, 1990.
Thiel, et al., Acutely Impaired Renal Function During Intravenous Administration of Cyclosporine A: A Cremaphore Side-Effect, Clinical Nephrology, vol. 25, Suppl. No. 1, pp. S40–S42, 1986.
Honbo, et al., The Oral Dosage Form of FK–506, Transplantation Proceedings, vol. XIX, No. 5, Suppl. 6, pp. 17–22, 1987.
Stepkowski, et al., Rapamycin, A Potent Immunosuppressive Drug for Vascularized Heart, Kidney, and Small Bowel Transplantation in the Rat, Transplantation, vol. 51, No. 1, pp. 22–24, 1991.
Kahan, et al., Synergistic Interactions of Cyclosporine and Rapamycin to Inhibit Immune Performances of Normal Human Peripheral Blood Lymphocytes In Vitro, Transplantation, vol. 51, No. 1, pp. 232–237, 1991.
Intl. Pharm. Abstracts—FK—506, Immunosuppressant for the 1990s, Macleod, et al., Lancet, 337, pp. 25–27, Jan. 5, 1991.
Intl. Pharm. Abstracts, FK–506: Discussion of a New Investigationsl Drug, C. G. Forde, ASHP Midyear Clinical Meeting, 25, p. 446D, Dec. 1990.
Intl. Pharm. Abstracts, FK–506, Kidney Transplantation Under FK 506, Starzl, et al., JAMA, 264, pp. 63–67, Jul. 4, 1990.
Intl. Pharm. Abstrcts–FK–506 In Steroid—Resistant Focal Sclerosing Glomerulonephritis of Childhood, McCauley, et al., Lancet, 335, p. 674, Mar. 17, 1990.
Intl. Pharm. Abstracts, New Drug Could Replace Cyclosporin in Transplant Drug Therapy, Anon, Am. Pharm. NS, 30, 16, Jan. 1990.
Intl. Pharm. Abstracts, Treatment of Cyclosporin Induced Hemolytic–Uremic Syndrome with FK–506, McCauley, et al., Lancet, 2, 1516, Dec. 23–30, 1989.
Intl. Pharm. Abstracts–FK–506 for Liver, Kidney, and Pancreas Transplantation; Starzl, et al., Lancet, 2, 1000–1004, Oct. 28, 1989.

*Primary Examiner*—Phyllis G. Spivack
*Attorney, Agent, or Firm*—Steven R. Eck

[57] ABSTRACT

The present invention provides novel oral rapamycin formulations which have, per 100 ml of the formulation, from about 0.01 grams to about 5.0 grams of rapamycin, from about 0.05% to about 10% by volume of surfactant, and from about 75% to about 99.95% by volume of a solution of phospholipid or lecithin in which the phospholipid or lecithin therein is 40% to 75% by weight.

14 Claims, No Drawings

RAPAMYCIN FORMULATIONS FOR ORAL ADMINISTRATION

This application is a continuation-in-part of Ser. No. 08/129,529, now abandoned, filed Sep. 30, 1993.

This invention relates to formulations or compositions containing rapamycin, or pharmaceutically acceptable salts of rapamycin, which are useful in oral administrations for inducing immunosuppression and for treating transplantation rejection, host vs. graft disease, autoimmune diseases, diseases of inflammation, solid tumors, fungal infections, adult T-cell leukemia/lymphomas and hyperproliferative vascular disorders.

BACKGROUND OF THE INVENTION

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

U.S. Pat. No. 5,100,899 (Calne) discloses methods of inhibiting transplant rejection in mammals using rapamycin and derivatives and prodrugs thereof. Other chemotherapeutic agents listed for use with rapamycin are azathioprine, corticosteroids, cyclosporin (and cyclosporin A), and FK-506, or any combination thereof.

The primary immunosuppressive agent presently used for inhibiting rejection in the allograft transplantation of organs in man is cyclosporine (Sandimmune®). Cyclosporine is a cyclic polypeptide consisting of 11 amino acids. The intravenous injectable formulation of Sandimmune® (IV) is a sterile ampul containing, per ml, 50 mg of cyclosporine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physicians' Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued January 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

The *Physicians' Desk Reference* (45th ed., 1991, p. 2119, Medical Economics Company, Inc.) lists cyclosporine under the Sandimmune® tradename as available in 25 mg and 100 mg strength capsules and as an oral solution in 50 ml bottles. The 25 mg capsules contain 25 mg cyclosporine, USP, and alcohol, USP dehydrated, at a maximum of 12.7% by volume. The 100 mg capsules contain cyclosporine, USP, 100 mg and alcohol, USP dehydrated, at a maximum 12.7% by volume. Inactive ingredients in the oral capsules are corn oil, gelatin, glycerol, Labrafil M 2125 CS (polyoxyethylated glycolysed glycerides), red iron oxide, sorbitol, titanium dioxide, and other ingredients. The oral solution is available in 50 mg bottles containing cyclosporine, USP, 100 mg and Ph. Helv. alcohol at 12.5% by volume dissolved in olive oil, Ph. Helv./Labrafil M 1944 CS (polyoxyethylated oleic glycerides) vehicle which must be diluted further with milk, chocolate milk or orange juice before oral administration.

Azathioprine (available from Burroughs Wellcome Co., Research Triangle Park, N.C., under the tradename Imuran®) is another orally administered immunosuppressive agent prescribed alone or in conjunction with other immunosuppressive agents. The *Physicians' Desk Reference* (45th ed., 1991, pp. 785–787, Medical Economics Company, Inc.) lists azathioprine as 6-[1-methyl-4-nitroimidazol-5-yl)thio] purine, which is provided for oral administration in scored tablets containing 50 mg azathioprine and the inactive ingredients lactose, magnesium stearate, potato starch, povidone, and stearic acid.

DESCRIPTION OF THE INVENTION

Methods of drug delivery are designed to deliver an acceptable dosage of the medication to the patient. In the case of oral formulations, it is highly desirable to provide a dosage form which meets this criteria and which can be effectively administered, preferably self-administered, in either clinical or non-clinical situations. The present invention concerns formulations useful in the oral administration of rapamycin. Rapamycin has been shown to possess immunosuppressive, antifungal and antiinflammatory activity in vivo and to inhibit thymocyte proliferation in vitro. Therefore, these formulations are useful in the treatment of *Candida albicans* infections, diseases of inflammation and transplant rejection autoimmune diseases, including lupus, rheumatoid arthritis, diabetes melitus, multiple sclerosis, etc.

Because the formulations disclosed herein contain rapamycin, they are considered to have antitumor, antifungal and antiproliferative activities. As such, the formulations of this invention are useful in the treatment of transplantation rejection, such as heart, kidney, liver, bone marrow and skin transplants; autoimmune diseases such as lupus, rheumatoid arthritis, diabetes mellitus, myasthenia gravis and multiple sclerosis; diseases of inflammation such as psoriasis, dermatitis, eczema, seborrhea, inflammatory bowel disease and eye uveitis; solid tumors; fungal infections; and hyperproliferative vascular diseases, such as restenosis. The present invention, therefore, also provides formulations useful for inducing immunosuppression in a mammal in such need. Such inducements would comprise administering to said mammal an immunosuppressive amount of one or more of the formulations discussed herein.

The formulations of the present invention may be produced as a one component, ready to use solution of rapamycin in a non-aqueous system consisting of a solvent, surfactant and a phospholipid solution to produce an acceptable dosage form for chronic use in association with immunosuppressant therapy, as well as antitumor, antifungal and antiproliferative activities. The one component system may be adjusted to eliminate the solvent in cases where the drug concentration can be solubilized in the remaining ingredients. The invention may also be produced alternatively as a two component system either comprised of a dry component fill of 100% rapamycin and diluent or a drug concentrate and diluent. Other filler materials, such as lactose or mannitol, may be used as a portion of the dry component of such systems.

In general, the formulations or compositions of the present invention include those containing combinations of a) rapamycin, b) surfactant, and c) lecithin or phospholipid solution in the following concentrations (per 100 ml formulation);

a) rapamycin at a concentration of from about 0.01 grams to about 5.0 gram per 100 ml; and b) a solvent system comprising:

i) Surfactant at a concentration of from about 0.05 ml to about 10 ml per 100 ml; and ii) from about 75 to about 99.95 ml per 100 ml of a lecithin or a phosholipid solution containing from about 40 to about 75 percent of lecithin or phospholipid by weight in one or more suitable solvents.

More preferred formulations of the present invention include those having the following concentration (per 100 ml formulation):

a) rapamycin at a concentration of from about 0.03 grams to about 1.0 gram per 100 ml;

b) Surfactant at a concentration of from about 0.10 ml to about 5 ml per 100 ml; and c) from about 90 ml to about 99.9 ml per 100 ml of a lecithin or a phosholipid solution containing from about 40 percent to about 70 percent by weight of lecithin or phospholipid in one or more suitable solvents.

A most preferred formulation of the present invention includes those formulations having concentrations of ingredients within the following ranges:

a) rapamycin at a concentration of from about 0.05 grams to about 0.5 grams per 100 ml;

b) Surfactant at a concentration of from about 0.5 ml to about 5 ml per 100 ml; and c) from about 95 to about 99.5 ml per 100 ml of a lecithin or a phospholipid solution containing from about 40 to about 60 percent by weight of lecithin or phospholipid in one or more suitable solvents.

The rapamycin dosage requirements for these formulations may vary depending upon the severity of the symptoms presented and the particular subject being treated. Projected daily oral dosages of the compounds of this invention, per kilogram of patient body weight, would be 0.005–75 mg/kg, preferably between 0.01–50 mg/kg, and more preferably between 0.05–10 mg/kg.

Treatment will generally be initiated with small dosages less than the optimum dose of the compound. Thereafter the dosage is increased until the optimum effect under the circumstances is reached. Precise dosages will be determined by the administering physician based on experience with the individual subject treated. In general, the formulations of this invention are most desirably administered at a concentration that will afford effective results without causing any harmful or deleterious side effects.

The present formulations may be administered to the patient by the means generally used for oral liquid medications. They may be taken, by themselves, or they may be dispersed in a liquid, such as water or juices. The formulations may also be capsulized, such as in pharmaceutically acceptable starch capsules or soft elastic gelatin (SEG) capsules. Rapamycin oral may be dispersed into water for dosing in the range of about 1 part of formula into about 9 parts water downward to about 1 part of formula into about 499 parts water by mixing for a minimum of about 60 seconds. This dispersion may be used over about a 1 hour period with mixing prior to dosing.

A number of solvents, other than those listed below, can be used to solubilize the drug(s) of the formulation covered herein. These include, but are not limited to, dimethylacetamide, ethanol, dimethylformamide, glycerin, polyethylene glycol, t-butanol, and propylene glycol. It is understood that the amounts of these solvents can be raised in conjunction with the drug concentration(s). Alternately, the amounts of the solvents can be reduced in conjunction with the drug concentrations and, if drug solubility permits, the lecithin, alone, can act as the solvent.

Surfactants that may be used with the present formulations include, but are not limited to, Polysorbate 20 (polyoxyethylene 20 sorbitan monolaurate), Polysorbate 60, Span 80® Sorbitan Oleate, a product of ICI Americas, Wilmington, Del., the Cremophor® surfactants produced by the BASF Corporation, Parsippany, N.J., and Polysorbate 80, which is defined by the Merck Index, 11th Edition, published by Merck & Co., Inc., Copyright 1989, on page 1254 as Sorbitan mono-9-octadecenoate poly(oxy-1,2-ethanediyl) derivatives, polyoxyethylene (20) sorbitan mono-oleate, Sorbitan mono-oleate polyoxyethylene, Softate, Tween 80, among others, and indicates an oleate ester of sorbitol and its anhydrides copolymerized with approximately 20 moles of ethylene oxide for each mole of sorbitol and sorbitol anhydrides. Polysorbate 80 is the surfactant preferred for use with the present invention.

A number phospholipid solutions may be used in the present formulations. It is preferred that the phospholipid solution of the present formulations comprises a lecithin solution. Lecithin is a general term for phosphatidylcholine or a mixture of various diglycerides of stearic, palmitic, and oleic acids, linked to the choline ester of phosphoric acid. Various types of lecithin or lecithin sourced products (such as separated phospholipids), either alone or mixed with various solvents, can be used as the final ingredient of the formulations mentioned above. These lecithin ingredients can include, for example, Alcolec® lecithin, produced by the American Lecithin Company, Danbury, Conn., Phosal 50 PG propylene glycol and lecithin, Phosal 50 MCT phosphatidylcholine and medium chained triglycerides, and Phospholipan 90® lecithin, all of which are produced by Nattermann Phospholipid GMBH, Colone, Germany, the Centrophil® and Centrophase® lecithins produced by Central Soya, Fort Wayne, Ind. It is preferred that the phospholipid solutions used in the present formulation have at least a 50% concentration of phospholipid. More particularly, it is preferred that the phospholipid solutions used with the present formulations be lecithin products or solutions having at least 50% phosphatidylcholine. It is also preferred that the phospholipid solution comprise a phospholipid in propylene glycol.

It is also understood that the present formulations may be used with other ingredients used with conventional oral formulations such as, but not limited to, flavor enhancers, coloring agents, adjuvants, antifungal agents, antibacterial agents, etc.

It is contemplated that when the formulations of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, cyclosporin A, FK-506, OKT- 3, and ATG. By combining one or more of the formulations of the present invention with such other drugs or agents for inducing immunosuppression or treating inflammatory conditions, lesser amounts of each of the agents may be required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The formulations of the present invention are exemplified, but not limited by, the preferred formulations and processes described below:

EXAMPLES

Example 1

Rapamycin Oral at 1 mg/ml

A rapamycin oral formulation at a concentration of 1 mg/ml can be formulated from the following active and inactive ingredients by the procedural steps which follow:

|  | Conc. | Input | Batch Formula 10,000 bottles |
|---|---|---|---|
| Active Ingredient: Rapamycin @ 100% Inactive Ingredients: | 1.00 mg/ml | 0.025 g | 0.250 kg |
| Polysorbate 80, NF | 10.8 mg/ml | 0.270 g | 2.700 kg |
| Phosal 50 PG ® propylene glycol and lecithin q.s. ad | 1.00 ml | 25.0 ml | 250.0 L |
|  | or 1.005 gm or | 25.125 g | 251.25 kg |

Density of the Final Formulation - 1.005 g/ml

If the potency of the rapamycin is less than 100%, the input must be adjusted to achieve the claimed potency.

Method of Manufacture

Procedure:
1. Weigh the rapamycin into a suitable container.
2. Add the Polysorbate 80 to the container in step #1
3. Adjust to the final volume with Phosal 50 PG.
4. Mix until the rapamycin is dissolved.
5. Fill 25 ml±1.25 ml (25.125 g±1.256 g) into each one ounce amber glass bottle. It is preferable to seal with a child resistant cap.

For improved wettability and ease of solution, an alternative order of addition of the ingredients and amounts presented above is as follows:
1. Polysorbate 80.
2. A portion of the Phosal 50 PG propylene glycol and lecithin.
3. Rapamycin.
4. The remaining Phosal 50 PG propylene glycol and lecithin.

The rapamycin in these formulations may also be comminuted by use of a mill or mortar and pestle and passed through an 80 mesh screen.

Example 2

Rapamycin Oral at 5 mg/ml

A rapamycin oral formulation at a concentration of 5 mg/ml can be formulated from the following active and inactive ingredients by the procedural steps which follow:

|  | Conc. | Input | Batch Formula 10,000 bottles |
|---|---|---|---|
| Active Ingredient: Rapamycin @ 100% Inactive Ingredients: | 5.00 mg | 0.125 g | 1.250 kg |
| Polysorbate 80, NF | 10.8 mg | 0.270 g | 2.70 kg |
| Phosal 50 PG propylene glycol and lecithin q.s. ad | 1.00 ml | 25.0 ml | 250.0 L |
|  | or 1.005 gm or | 25.125 g or | 251.25 kg |

Density of the Final Formulation - 1.005 g/ml.

If the potency of the rapamycin is less than 100%, the input must be adjusted to give the claimed potency.

The procedural steps for formulation and storage of the 5 mg/ml oral rapamycin formulation are the same as those listed in Example 1, as are the alternative order of addition of ingredients and the methods of comminution.

Example 3

The formulation of this Example 3 was produced using the ingredients which follow and the methods indicated below:

| Ingredients | Amount |
| --- | --- |
| Rapamycin @ 100% up to | 1.0 gm |
| Polysorbate 80, NF | 1.0 ml or 1.08 gm |
| Phosal 50 PG lecithin and propylene glycol q.s. | 100 ml or 100.5 gm |

Method of Formulation

1. Weigh the rapamycin into a suitable container.
2. Add the Polysorbate 80 into the container of Step #1.
3. Adjust to the final volume with Phosal 50 PG® propylene glycol and lecithin.
4. Mix until a solution results.

Alternatively, this formula can be packaged in a suitable container or encapsulated into a capsule.

Cynomolgus monkeys were administered a formulation of Example 3, above, at a dose of 0.25 mg/kg of rapamycin and the following serum concentrations were determined at the indicated time after dosing:

| Rapamycin Concentration in Monkey Serum Dosed Orally as a Dispersion of 0.25 mg/kg | | | | | | |
| --- | --- | --- | --- | --- | --- | --- |
| Time | Rapamycin Concentrate (µg/ml) | | | | | |
| (hrs) | A | B | C | D | E | F |
| 0 | 0.000 | 0.000 | 0.000 | 0.000 | 0.000 | 0.000 |
| .25 | 0.012 | 0.001 | 0.005 | 0.000 | 0.000 | 0.000 |
| .50 | 0.014 | 0.000 | 0.024 | 0.004 | 0.000 | 0.003 |
| 1 | 0.011 | 0.002 | 0.021 | 0.006 | 0.003 | 0.004 |
| 2 | 0.005 | 0.019 | 0.008 | 0.004 | 0.007 | 0.003 |
| 4 | 0.002 | 0.006 | 0.007 | 0.003 | 0.006 | 0.002 |
| 8 | 0.002 | 0.004 | 0.005 | 0.003 | 0.002 | 0.001 |
| 12 | 0.001 | 0.002 | 0.003 | 0.002 | 0.001 | 0.001 |
| 24 | 0.001 | 0.002 | 0.001 | 0.001 | 0.002 | 0.001 |
| 36 | 0.000 | 0.002 | 0.001 | 0.001 | 0.000 | 0.000 |

Example 4

| Formula | Ingredients |
| --- | --- |
| Rapamycin @ 100% up to | 2.5 grams |
| Polysorbate 80, NF | 5.0 ml or 5.4 gm |
| Absolute Ethanol | 12.67 ml or 10.0 gm |
| Phosal 50 PG lecithin and propylene glycol q.s. | 100 ml |

This formulation can be produced by the following steps:
1. Weigh the rapamycin into a suitable container
2. Add the absolute ethanol to the container in Step #1. Mix until dissolved.
3. Add the polysorbate 80 to the container in Step #2. Mix until uniform.
4. Add Phosal 50 PG lecithin and propylene glycol to adjust to the final volume.
5. Mix until uniform.

Alternatively, this formula can be packaged in a suitable container or encapsulated into a capsule.

Cynomolgus monkeys were administered the formulation above at a dose of 0.25 mg/kg of rapamycin and the following serum concentrations were determined at the indicated time after dosing.

| Rapamycin Concentration in Monkey Serum Dosed Orally in a Dispersion at 0.25 mg/kg | | | | | | |
| --- | --- | --- | --- | --- | --- | --- |
| Time | Rapamycin Concentration (µg/ml) Monkey No. | | | | | |
| (hr) | A | B | C | D | E | F |
| 0 | 0.000 | 0.000 | 0.000 | 0.000 | 0.000 | 0.000 |
| .25 | — | 0.025 | 0.007 | 0.010 | 0.007 | 0.003 |
| .50 | 0.008 | 0.030 | 0.027 | 0.004 | 0.016 | 0.012 |
| 1 | 0.050 | 0.022 | 0.051 | 0.006 | 0.051 | 0.011 |
| 2 | 0.026 | 0.026 | 0.026 | 0.019 | 0.025 | 0.006 |
| 4 | 0.008 | 0.011 | 0.020 | 0.005 | 0.018 | 0.006 |
| 8 | 0.008 | 0.004 | 0.009 | 0.003 | 0.011 | 0.003 |
| 12 | 0.004 | 0.002 | 0.006 | 0.005 | 0.007 | 0.003 |
| 24 | 0.002 | — | 0.004 | 0.002 | 0.004 | 0.001 |
| 36 | 0.000 | 0.003 | 0.003 | 0.001 | 0.003 | 0.002 |

| Rapamycin Concentration in Monkey Serum Dosed Orally in SEG Capsules at 0.25 mg/kg | | | | | | |
| --- | --- | --- | --- | --- | --- | --- |
| Time | Rapamycin Concentration (µg/ml) Monkey No. | | | | | |
| (hr) | A | B | C | D | E | F |
| 0 | 0.000 | 0.000 | 0.000 | 0.000 | 0.000 | 0.000 |
| .25 | 0.000 | 0.000 | 0.000 | 0.000 | 0.001 | 0.001 |
| .50 | 0.000 | 0.000 | 0.000 | 0.000 | 0.010 | 0.006 |
| 1 | 0.030 | 0.013 | 0.001 | 0.000 | 0.019 | 0.005 |
| 2 | 0.014 | 0.024 | 0.014 | 0.002 | 0.014 | 0.005 |
| 4 | 0.013 | 0.011 | 0.003 | 0.006 | 0.015 | 0.004 |
| 8 | 0.007 | 0.004 | 0.002 | 0.002 | 0.007 | 0.002 |
| 12 | 0.005 | 0.003 | 0.001 | 0.001 | 0.006 | 0.001 |
| 24 | 0.003 | 0.001 | 0.001 | 0.001 | 0.003 | 0.001 |
| 36 | 0.002 | 0.001 | 0.001 | 0.000 | 0.001 | 0.000 |

Example 5

The oral formulations of this invention, such as those disclosed in Example 1 above, may also be prepared in encapsulated forms, such as formulations within starch or SEG capsules. The following procedure describes a method which may be utilized to prepare such encapsulated formulations.

Procedure:
1) Add to a container, NF, the Polysorbate 80.
2) Add to the Polysorbate 80 of Step #1 80% of the the required Phosal 50 PG.
3) Weigh the rapamycin component of the formulation into the container of Step #2.
4) Adjust to the final formulation weight with Phosal 50 PG.
5) Establish a nitrogen atmosphere over the formulation and maintain until the capsules are filled.
6) Mix the formulation until the rapamycin is dissolved.
7) Pass the formulation solution through a particulate (such as a 100 mesh screen) or scintered glass filter.
8) Fill 0.50 ml of the Step #7 material into capsule shells using an automatic syringe dispensing unit and seal the capsule.

9) Package the filled capsules upon completion of encapsulation. An example of a preferred package is a conventional blister package with a perforable metal foil backing.
10) Store the finished encapsulated product at refridgerated conditions (2°–8° C.) protected from light.

The primary capsule sealant for the starch capsule may be a 5% Dextrin, NF, aqueous solution. It is preferable to heat purified water to 50°–60° C. prior to compounding to facilitate dissolution of the Dextrin. Prior to use it is also preferable to filter the the Dextrin solution through a suitable particulate filter.

Bioavailability a) Cynomolgus monkeys were administered a starch and SEG encapsulated formulation of Example 3, above, at a dose of 0.25 mg/kg of rapamycin and the following serum concentrations were determined at the indicated time after dosing:

Rapamycin Concentration in Monkey Serum Dosed Orally in Starch Capsules 0.25 mg/kg

| Time | Rapamycin Concentrate (μg/kg) | | | | | |
|---|---|---|---|---|---|---|
| (hrs) | A | B | C | D | E | F |
| 0 | 0.000 | 0.000 | 0.000 | 0.000 | 0.000 | 0.000 |
| .25 | 0.000 | 0.000 | 0.000 | 0.000 | 0.000 | 0.000 |
| .50 | 0.000 | 0.000 | 0.005 | 0.000 | 0.005 | 0.000 |
| 1 | 0.029 | 0.004 | 0.026 | — | 0.008 | 0.000 |
| 2 | 0.011 | 0.019 | 0.032 | 0.000 | 0.011 | 0.004 |
| 4 | 0.007 | 0.009 | 0.011 | 0.002 | 0.007 | 0.002 |
| 8 | 0.004 | 0.003 | 0.004 | 0.002 | 0.005 | 0.002 |
| 12 | 0.002 | 0.001 | — | 0.001 | 0.002 | 0.001 |
| 24 | 0.001 | 0.000 | 0.002 | 0.001 | 0.001 | 0.000 |
| 36 | 0.000 | 0.000 | 0.000 | 0.000 | 0.000 | 0.000 |

Rapamycin Concentration in Monkey Serum Dosed Orally in SEG Capsules at 0.25 mg/kg

| Time (hrs) | A | B | C | D | E | F |
|---|---|---|---|---|---|---|
| 0 | 0.000 | 0.000 | 0.000 | 0.000 | 0.000 | 0.000 |
| .25 | 0.005 | 0.002 | 0.001 | 0.001 | 0.001 | 0.002 |
| .50 | 0.001 | 0.001 | 0.002 | 0.002 | 0.001 | 0.001 |
| 1 | 0.043 | 0.022 | 0.019 | 0.002 | 0.003 | 0.012 |
| 2 | 0.027 | 0.030 | 0.019 | 0.002 | 0.010 | 0.008 |
| 4 | 0.012 | 0.012 | 0.015 | 0.009 | 0.011 | 0.006 |
| 8 | 0.008 | 0.006 | 0.009 | 0.004 | 0.006 | 0.003 |
| 12 | 0.008 | 0.004 | 0.006 | 0.002 | 0.005 | 0.002 |
| 24 | 0.006 | 0.003 | 0.005 | 0.001 | 0.002 | 0.001 |
| 36 | 0.002 | 0.001 | 0.002 | 0.001 | 0.002 | 0.001 | b) 3 mg starch encapsulated formulations containing rapamycin at a concentration of 6 mg/ml, prepared as described above, were administered to 14 healthy male human volunteers between the ages of 18 and 45, from whom blood samples were drawn at the time intervals indicated in the table below. The rapamycin blood samples were assayed for whole blood rapamycin concentration using a validated (ESP)-HPLC-MS method.

| Time Interval Following Administration (Hours) | Blood Concentration (conc. = ng/ml) |
|---|---|
| 0.33 | 0.41 |
| 0.67 | 6.53 |
| 1 | 8.57 |
| 2 | 8.27 |
| 3 | 5.54 |
| 4 | 3.96 |
| 5 | 3.10 |
| 8 | 1.93 |
| 12 | 1.47 |
| 18 | 1.05 |
| 24 | 0.80 |
| 48 | 0.54 |

COMPARATIVE EXAMPLES

Comparative Example 1

The following Comparative Examples illustrate traditional solutions, suspensions or emulsions that are used to administer drugs which have poor water solubilities, and which have now been applied to the administration of rapamycin, as well as the blood levels of rapamycin provided by such administrations.

This first standard formulation utilizes a diluent having the ingredients and made by the steps listed below:

| Diluent for Oral Rapamycin Formulations | |
|---|---|
| Ingredients | Amounts |
| Polysorbate 80, NF | 5.0 ml |
| 0.5M Citric Acid (pH 4) q.s. | 100 ml |

Manufacturing Directions

1. Prepare a 0.5M Citric Acid solution.
2. Adjust the pH of the solution in Step #1 to 4.0 using 50% w/w NaOH.
3. Place the Polysorbate 80 into a suitable container.
4. QS to 100 ml with the solution from step #2.
5. Mix until uniform.

This diluent may be used to create an oral rapamycin formulation by mixing rapamycin with the diluent as indicated below:

| Ingredients | Amounts |
|---|---|
| Rapamycin Micronized @ 100% up to | 5.0 gm |
| Diluent for Oral Rapamycin q.s. | 100 ml |

Manufacturing Directions

1. Weigh the rapamycin into a suitable container.
2. QS with the diluent for rapamycin.
3. Mix until uniform.

Cynomolgus monkeys were administered the above formulation at a dose of 50 mg/kg of rapamycin and the following serum concentrations were determined at the indicated time after dosing.

| Rapamycin Concentration in Monkey Serum Dosed Orally with 50 mg/kg Rapamycin Oral Suspension | | | |
|---|---|---|---|
| Time | Rapamycin Concentration (µg/ml) Monkey No. | | |
| (hr) | A | B | C |
| 0 | BDL | BDL | BDL |
| 1 | BDL | BDL | BDL |
| 2 | BDL | BDL | BDL |
| 3 | BDL | BDL | BDL |
| 4 | BDL | BDL | BDL |
| 6 | BDL | BDL | BDL |
| 9 | BDL | BDL | BDL |
| 12 | BDL | BDL | BDL |

BDL = Below detection limit (detection limit = 0.006 µg/ml)

Comparative Example 2

A second traditional formulation, with rapamycin as the active ingredient, can be produced by the using the following ingredients in the steps below:

| Rapamycin Oral | |
|---|---|
| Ingredients | Amount |
| Rapamycin @ 100% | 5.0 gm |
| Dimethylacetamide | 10.0 gm |
| Absolute Ethanol | 10.0 gm |
| Miglyol 812 | q.s. 100 ml |

Procedure:
1. Place rapamycin into a suitable container.
2. Add the dimethylacetamide and ethanol to the container in Step #1 and mix until a solution results.
3. QS with Miglyol 812 and mix until uniform.
4. Filter sample through a 0.2 micron Teflon filter.

Cynomolgus monkeys were administered this second comparative formulation at a dose of 50 mg/kg of rapamycin and the following serum concentrations were determined at the indicated time after dosing.

| Rapamycin Concentration in Monkey Serum Dosed Orally with 50 mg/kg Rapamycin Oral Solution | | | |
|---|---|---|---|
| Time | Rapamycin Concentration (µg/ml) Monkey No. | | |
| (hr) | A | B | C |
| 0 | BDL | BDL | BDL |
| 1 | BDL | BDL | BDL |
| 2 | BDL | BDL | BDL |
| 3 | BDL | BDL | BDL |
| 4 | BDL | BDL | BDL |
| 6 | BDL | BDL | BDL |
| 9 | BDL | BDL | BDL |
| 12 | BDL | BDL | BDL |

BDL = Below detection limit (detection limit = 0.006 µg/ml)

Comparative Example 3

A third comparative formulation was produced using the ingredients and method described below:

| Rapamycin Oral Emulsion at 50 mg/ml Formula: | |
|---|---|
| Ingredients | Amount |
| Rapamycin @ 100% | 5.0 gm |
| Dimethylacetamide | 10 ml |
| Olive Oil | q.s. 100 ml |

Procedure:
1. Place the rapamycin into a suitable container.
2. Add the dimethylacetatmide to the container in Step #1 and mix until clear.
3. QS with Olive Oil and mix until homogenous.

Cynomolgus monkeys were administered this second comparative formulation at a dose of 50 mg/kg of rapamycin and the following serum concentrations were determined at the indicated time after dosing.

| Rapamycin Concentration in Monkey Serum Dosed Orally with 50 mg/kg Rapamycin Oral Emulsion | | | |
|---|---|---|---|
| Time | Rapamycin Concentration (µg/ml) Monkey No. | | |
|  | A | B | C |
| 0 | BDL | BDL | BDL |
| 20 min | BDL | BDL | BDL |
| 40 min | BDL | BDL | BDL |
| 80 min | BDL | BDL | BDL |
| 3 hr | BDL | BDL | BDL |
| 6 hr | BDL | 0.110* | BDL |
| 12 hr | BDL | BDL | BDL |
| 24 hr | BDL | BDL | BDL |

BDL = Below detection limit (detection limit = 0.006 µg/ml)
*NOTE: Assay result obtained from test lab appears aberent.

What is claimed:

1. A composition comprising, per 100 ml of composition, from about 0.01 gram to about 5.0 grams of rapamycin, and a solvent system, said solvent system comprising from about 0.05 to 10% by volume of a surfactant, and from about 75 to 99.95% by volume of a phospholipid solution in which the phospholipid therein is 40% to 75% by weight.

2. The composition of claim 1 wherein the phospholipid solution is a lecithin solution.

3. A composition of claim 1 containing from about 0.03 gram to about 1.0 gram of rapamycin per 100 ml, and a solvent system containing from about 0.10 ml to about 5 ml of surfactant per 100 ml, and from about 90 to about 99.95 ml of a phosholipid solution, the solution containing from about 40% to about 70% by weight of phospholipid in a suitable solvent, per 100 ml.

4. The composition of claim 1 which contains, per 100 ml composition, from about 0.03 gram to about 0.8 grams rapamycin, from about 0.10 ml to about 5 ml of surfactant, and from about 95 to about 99.9 ml of a 50% phospholipid solution.

5. The composition of claim 1 which contains, per 100 ml composition, from about 0.05 grams to about 0.5 grams rapamycin, from about 0.5 ml to about 5 ml of surfactant, and from about 95 to about 99.5 ml of a 50% phospholipid solution.

6. The composition of claim 1 which contains, per 25 ml composition, 0.025 g of rapamycin, 0.270 g of surfactant, and a 50% phospholipid solution q.s. to 25 ml.

7. The composition of claim 1 which contains, per 25 ml composition, 0.125 g of rapamycin, 0.270 g of surfactant, and a 50% phospholipid solution q.s. to 25 ml.

8. The composition of claim 1 which contains, per 100 ml composition, 1.0 g of rapamycin, 1.0 ml of surfactant, and a 50% phospholipid solution q.s. to 100 ml.

9. The composition of claim 1 which is contained within a pharmaceutically acceptable starch capsule.

10. The composition of claim 1 which is contained within a pharmaceutically acceptable gelatin capsule.

11. The composition comprising, per 100 ml composition, from about 0.01 grams to about 5.0 grams of rapamycin and a solvent system comprising:

a) from about 0.05% to about 10% by volume of surfactant, b) from about 0.1% to about 50% by volume of absolute ethanol, and c) from about 40% to about 99.85% by volume of a phospholipid solution, the phospholipid solution being from about 40% to about 75% by weight phospholipid.

12. The composition of matter of claim 11 wherein the phospholipid solution is a lecithin solution.

13. The composition of claim 11 comprising, per 100 ml composition, from about 2.0 to about 3.0 grams of rapamycin and a solvent system comprising:

a) from about 3% to about 7.5% by volume of surfactant, b) from about 5% to about 20% by volume of absolute ethanol, and c) from about 40% to about 92% by volume of a phospholipid solution, the phospholipid solution being from about 40% to about 60% by weight phospholipid.

14. The composition of claim 11 comprising, per 100 ml composition, 2.5 grams of rapamycin, 5.0 ml of surfactant, about 12.67 ml of absolute ethanol, and a 50% phospholipid solution q.s to 100 ml.

* * * * *